United States Patent
Nakagawa

(10) Patent No.: US 8,664,437 B2
(45) Date of Patent: Mar. 4, 2014

(54) PROCESS FOR PRODUCING (METH) ACRYLIC ACID

(75) Inventor: Satoshi Nakagawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 76 days.

(21) Appl. No.: 13/377,657

(22) PCT Filed: Jun. 24, 2010

(86) PCT No.: PCT/JP2010/060752
§ 371 (c)(1),
(2), (4) Date: Dec. 12, 2011

(87) PCT Pub. No.: WO2011/001893
PCT Pub. Date: Jan. 6, 2011

(65) Prior Publication Data
US 2012/0088932 A1    Apr. 12, 2012

(30) Foreign Application Priority Data

Jul. 2, 2009  (JP) .................. 2009-158178

(51) Int. Cl.
*C07C 51/42*    (2006.01)
(52) U.S. Cl.
USPC ........................................................ 562/600
(58) Field of Classification Search
USPC ........................................ 562/400, 598, 600
See application file for complete search history.

(56) References Cited

U.S. PATENT DOCUMENTS

| | | | |
|---|---|---|---|
| 5,504,247 A * | 4/1996 | Saxer et al. .................. | 562/600 |
| 5,546,763 A | 8/1996 | Kikuchi et al. | |
| 5,935,534 A | 8/1999 | Umino et al. | |
| 2003/0149301 A1 | 8/2003 | Eck et al. | |

FOREIGN PATENT DOCUMENTS

| | | |
|---|---|---|
| CN | 1105014 | 7/1995 |
| JP | 7-48311 | 2/1995 |
| JP | 9-155101 | 6/1997 |

OTHER PUBLICATIONS

Business German Dictionary, Peter Collin Publishing, 1994.*
Extended European Search Report issued Dec. 7, 2012 in corresponding European Application No. 10794062.9.
International Search Report issued Sep. 14, 2011 in International (PCT) Application No. PCT/JP2010/060752, of which the present application is the national stage.
Office Action issued Jul. 30, 2013 in corresponding Chinese Application No. 201080025976.4, with English translation thereof.

* cited by examiner

*Primary Examiner* — Wu-Cheng Winston Shen
*Assistant Examiner* — Blaine G Doletski
(74) *Attorney, Agent, or Firm* — Wenderoth, Lind & Ponack, L.L.P.

(57) ABSTRACT

A process for producing (meth)acrylic acid, comprising the step of repeating a crystallization operation "n" times (providing "n" is an integer 2 or more) to produce purified (meth) acrylic acid from crude (meth)acrylic acid, wherein a (meth) acrylic acid solution is crystallized and the crystallized (meth)acrylic acid is melted to obtain a (meth)acrylic acid melt in the crystallization operation; wherein a constant amount $A_k$ of the (meth)acrylic acid solution is subjected to the $k^{th}$ crystallization operation (providing "k" is an integer 1 to n−1), and the (meth)acrylic acid melt obtained by the $k^{th}$ crystallization operation is utilized as the (meth)acrylic acid solution for the $k+1^{th}$ crystallization operation without being discharged from a crystallizer or is transferred from the crystallizer to a $k+1^{th}$ storage tank for storing the (meth)acrylic acid solution to be used in the $k+1^{th}$ crystallization operation depending on the stored amount of the $k+1^{th}$ storage tank.

4 Claims, 1 Drawing Sheet

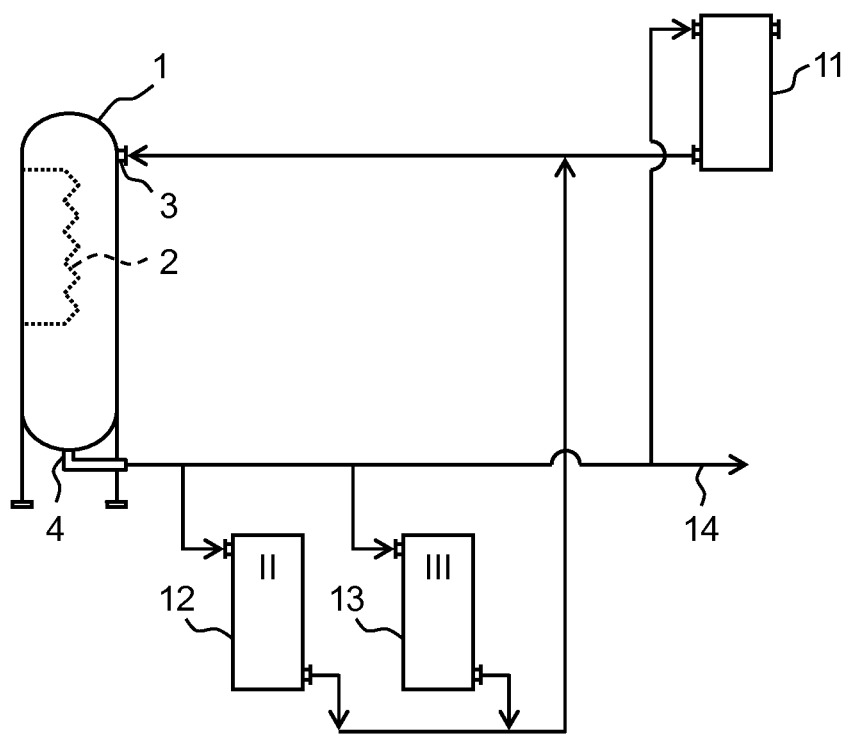

PROCESS FOR PRODUCING (METH) ACRYLIC ACID

TECHNICAL FIELD

The present invention relates to a process for producing (meth)acrylic acid having crystallization operations.

BACKGROUND ART

Conventionally, a process for industrially producing (meth)acrylic acid by gas-phase catalytic oxidation of a (meth)acrylic acid production raw material has been known. A (meth)acrylic acid-containing gas produced by a gas-phase catalytic oxidation reaction from the (meth)acrylic acid production raw material is, for example, collected by a liquid medium or condensed to be recovered as a crude (meth) acrylic acid solution, and then, the crude (meth)acrylic acid solution is purified by a method such as distillation, diffusion, extraction, crystallization, or the like.

For example, Patent Literature 1 discloses a method for purifying crude (meth)acrylic acid by repeating crystallization multiple times. In the method disclosed in Patent Literature 1, a liquid raw material stored in a $k^{th}$ storage tank is crystallized and then melted, a non-crystallized residual mother liquid is transferred to a $k-1^{th}$ storage tank, a melt is transferred to a $k+1^{th}$ storage tank, and then, a liquid raw material stored in the $k+1^{th}$ storage tank is crystallized.

CITATION LIST

Patent Literature

Patent Literature 1
Japanese Unexamined Laid-open Patent Application Publication No. 9-155101

SUMMARY OF INVENTION

Technical Problem

In the method disclosed in Patent Literature 1, since the whole amount of the melt obtained by crystallizing the liquid raw material in the $k^{th}$ storage tank is transferred to the $k+1^{th}$ storage tank, followed by performing the crystallization of the liquid raw material stored in the $k+1^{th}$ storage tank, the large amounts of the melt and the liquid raw material are transferred, that is inefficient. In addition, Patent Literature 1 does not disclose the idea of adjusting the amount of the liquid raw material fed to a crystallizer from the $k^{th}$ storage tank to be constant in the crystallization of the liquid raw material stored in the $k^{th}$ storage tank. Therefore, it is likely that the quality or recovered amount of the obtained melt varies.

The present invention has been achieved in view of the above circumstances, and the object of the present invention is to provide a process for producing (meth)acrylic acid that enables obtaining purified (meth)acrylic acid efficiently.

Solution to Problem

A process for producing (meth)acrylic acid of the present invention which solves the above problems comprises the step of repeating a crystallization operation "n" times (providing "n" is an integer 2 or more) to produce purified (meth) acrylic acid from crude (meth)acrylic acid, wherein a (meth) acrylic acid solution is crystallized and the crystallized (meth)acrylic acid is melted to obtain a (meth)acrylic acid melt in the crystallization operation; wherein a constant amount $A_k$ of the (meth)acrylic acid solution is subjected to the $k^{th}$ crystallization operation (providing "k" is an integer 1 or more and n−1 or less), and the (meth)acrylic acid melt obtained by the $k^{th}$ crystallization operation is utilized as the (meth)acrylic acid solution for the $k+1^{th}$ crystallization operation without being discharged from a crystallizer or is transferred from the crystallizer to a $k+1^{th}$ storage tank for storing the (meth)acrylic acid solution to be used in the $k+1^{th}$ crystallization operation in accordance with the following Rules (1) or (2):

Rule (1): when an amount of the (meth)acrylic acid melt obtained by the $k^{th}$ crystallization operation is $B_k$ and an amount of the (meth)acrylic acid solution stored in the $k+1^{th}$ storage tank is $A_{k+1}-B_k$ or more, the (meth)acrylic acid melt obtained by the $k^{th}$ crystallization operation is not discharged from the crystallizer and the (meth)acrylic acid solution from the $k+1^{th}$ storage tank is added to the (meth)acrylic acid melt obtained by the $k^{th}$ crystallization operation to be utilized as the (meth)acrylic acid solution for the $k+1^{th}$ crystallization operation; and Rule (2): when the amount of the (meth)acrylic acid solution stored in the $k+1^{th}$ storage tank is less than $A_{k+1}-B_k$, the (meth)acrylic acid melt obtained by the $k^{th}$ crystallization operation is transferred to the $k+1^{th}$ storage tank from the crystallizer.

In the producing process of the present invention, since the amount of the (meth)acrylic acid solution subjected to the $k^{th}$ crystallization operation is set to be a constant value $A_k$ and operation conditions is uniformed, it becomes easy to conduct the crystallization operation stably. Therefore, purity and recovered amount of the (meth)acrylic acid melt obtained at each stage is made uniform, and thus, it becomes easy to efficiently control the purity of the purified (meth)acrylic acid which is finally obtained.

Moreover, it becomes easy that the amount of (meth) acrylic acid solution to be subjected to the $k^{th}$ crystallization operation is efficiently adjusted to the constant value $A_k$ by following the above rules (1) and (2). Thus, it is possible to suppress the transferring amount of the (meth)acrylic acid melt between the crystallizer and the storage tank to a minimal necessary, resulting in suppressing energies required for pump power and the like which are related to the transfer of the (meth)acrylic acid melt. In addition, when the transferring amount of the (meth)acrylic acid melt is suppressed to a minimal necessary, it becomes possible to increase production amount due to reduction of transferring time of the (meth)acrylic acid melt, and the (meth)acrylic acid melt is easily prevented from inadvertent impurity incorporation. Therefore, the purified (meth)acrylic acid can be obtained efficiently by the crystallization operation and the purity of the obtained purified (meth)acrylic acid can be easily enhanced.

When the amount of the (meth)acrylic acid solution stored in the $k+1^{th}$ storage tank is less than $A_{k+1}-B_k$, it is preferred that the (meth)acrylic acid melt obtained by the $k^{th}$ crystallization operation is transferred to the $k+1^{th}$ storage tank from the crystallizer, followed by performing the $k^{th}$ or less ordinal crystallization operation in the crystallizer. Thereby, the (meth)acrylic acid solution subjected to the $k+2^{th}$ or more ordinal crystallization operation is prevented from being contaminated by the (meth)acrylic acid melt obtained by the $k^{th}$ crystallization operation, resulting in efficiently producing the purified (meth)acrylic acid.

When the amount of the (meth)acrylic acid solution stored in the $k+1^{th}$ storage tank is $A_{k+1}-B_k$ or more, it is preferred that the (meth)acrylic acid melt obtained by the $k^{th}$ crystallization operation is not discharged from the crystallizer and an amount $A_{k+1}-B_k$ of the (meth)acrylic acid solution from the $k+1^{th}$ storage tank is added to the (meth)acrylic acid melt obtained by the $k^{th}$ crystallization operation. Thereby, in the case of following the rule (1), the amount of the (meth)acrylic acid solution subjected to the $k+1^{th}$ crystallization operation can be efficiently adjusted to a constant value $A_{k+1}$.

Advantageous Effects of Invention

According to the process for producing (meth)acrylic acid of the present invention, purified (meth)acrylic acid can be obtained efficiently.

BRIEF DESCRIPTION OF THE DRAWINGS

FIG. 1 shows an example of a crystallization apparatus used in the producing process of the present invention.

DESCRIPTION OF THE PREFERRED EMBODIMENTS

A process for producing (meth)acrylic acid of the present invention is for producing purified (meth)acrylic acid from crude (meth)acrylic acid by repeating a crystallization operation "n" times (providing "n" is an integer 2 or more), wherein a (meth)acrylic acid solution is crystallized and the crystallized (meth)acrylic acid is melted to obtain a (meth)acrylic acid melt in the crystallization operation.

In every crystallization operation, the (meth)acrylic acid solution is crystallized and the crystallized (meth)acrylic acid is melted to obtain the (meth)acrylic acid melt. In the present invention, the crude (meth)acrylic acid is used as the (meth)acrylic acid solution which is subjected to the first crystallization operation, and the (meth)acrylic acid melt obtained by the $n^{th}$ crystallization operation is recovered as the purified (meth)acrylic acid.

No particular limitation is placed on the crude (meth)acrylic acid, and the crude (meth)acrylic acid can be any solution containing (meth)acrylic acid and an impurity thereof. Examples of the impurity include unreacted (meth)acrylic acid production raw materials, water, acetic acid, propionic acid, maleic acid, acetone, acrolein, furfural, formaldehyde, a condensation liquid medium and the like. The crude (meth)acrylic acid preferably has a (meth)acrylic acid concentration of 80 mass % or more.

In every crystallization operation, the (meth)acrylic acid is crystallized and melted, thereby obtaining the (meth)acrylic acid melt. In detail, the crystallization operation includes a crystallizing step of obtaining a (meth)acrylic acid crystal by crystallizing the (meth)acrylic acid solution and a melting step of obtaining the (meth)acrylic acid melt by melting the (meth)acrylic acid crystal. In addition, a sweating step of partially-melting the (meth)acrylic acid crystal and washing away impurities present between the crystals or on the surface of the crystal, may be performed for the purpose of enhancing the purity of the obtained (meth)acrylic acid melt.

The crystallization operation is properly performed by using a crystallizer. Any crystallizer can be used as long as the crystallizer is capable of crystallizing the (meth)acrylic acid solution and melting the crystallized (meth)acrylic acid to obtain the (meth)acrylic acid melt. Examples of the crystallizer includes, for example, a crystallizer provided with a heat-transfer surface, wherein the (meth)acrylic acid solution is crystallized and melted by heat exchange via the heat-transfer surface. In this crystallizer, (meth)acrylic acid is crystallized from the (meth)acrylic acid solution by heat exchange via the heat-transfer surface in the crystallizing step, thereby obtaining the (meth)acrylic acid crystal. In the melting step, the (meth)acrylic acid crystal is melted by heat exchange via the heat-transfer surface, thereby obtaining the (meth)acrylic acid melt.

As the crystallizer having the heat-transfer surface, an apparatus used as a heat exchanger generally can be employed. For example, a plate-type heat exchanger comprising a single plate or a plurality of plates stacked at intervals, wherein a medium-present part and a crystal-present part are alternately disposed while being separated by the plate; a multitubular (shell-and-tube) heat exchanger comprising a plurality of tubes in a vessel, wherein heat is exchanged between the interiors and exteriors of the tubes; a double-pipe heat exchanger comprising an outer pipe and an inner pipe disposed in the outer pipe, wherein heat is exchanged between the interior and exterior of the inner pipe; a coil heat exchanger comprising one coil-shaped tube disposed in a vessel, wherein heat is exchanged between the interior and exterior of the tube; a spiral plate exchanger comprising a center tube whose cross-section is divided into two parts and two heat exchanger plates winding the center tube in whorl, whereby two whorl-like paths are formed; or the like may be employed. A cross-sectional shape of the tubes used in the multitubular heat exchanger, the double-pipe heat exchanger, the coil heat exchanger and the spiral plate exchanger is not particularly limited.

In the case where the crystallization operation is conducted by using in the crystallizer having the heat-transfer surface, for example, the (meth)acrylic acid solution may be cooled by feeding a cooling medium to the crystallizer in the crystallizing step and the (meth)acrylic acid crystal may be heated by feeding a heating medium to the crystallizer in the sweating and melting steps. Cooling of the cooling medium and heating of the heating medium can be performed by a conventionally-known heat source device, and examples of the heat source device include, for example, a multitubular heat exchanger in which liquefied gas or steam is used as a heat source. In addition, a refrigerator which supplies both the cooling medium and the heating medium, such as an absorption refrigerator, a compression refrigerator, an adsorption refrigerator and the like, can be used as the heat source device. As the cooling medium and the heating medium, ethylene glycol aqueous solution, glycerin aqueous solution, methanol aqueous solution, or the like can be used.

In the crystallizing step, temperature of the heat-transfer surface, which corresponds to temperature of the cooling medium in the case of using the cooling medium, is not particularly limited as long as it is lower than the melting point of the (meth)acrylic acid solution; however, the temperature is preferably 0° C. or lower, and more preferably −5° C. or lower for efficiently crystallizing the (meth)acrylic acid solution. Meanwhile, the lower limit of the temperature is not particularly limited.

In the sweating and melting steps, temperature of the heat-transfer surface, which corresponds to temperature of the heating medium in the case of using the heating medium, is not particularly limited as long as it is higher than the melting point of the (meth)acrylic acid crystal; however, the temperature is preferably 20° C. or higher, and more preferably 25° C. or higher for efficiently melting the (meth)acrylic acid crystal. On the other hand, concerning the upper limit of the temperature, the temperature is preferably 45° C. or lower, and more preferably 40° C. or lower for preventing polymerization reaction of (meth)acrylic acid and enhancing the purity or yield of the obtained (meth)acrylic acid melt.

In the producing process of the present invention, the crystallization operation is repeated "n" times to produce purified (meth)acrylic acid from crude (meth)acrylic acid, wherein the "n" is an integer 2 or more. Repeating the crystallization operation multiple times allows obtaining the purified (meth) acrylic acid with higher purity. The number of repeating the crystallization operation is preferably 3 or more in consideration of the producing efficiency and purity of the obtained purified (meth)acrylic acid.

In the producing process of the present invention, the (meth)acrylic acid melt obtained by the $k^{th}$ crystallization operation is utilized as the (meth)acrylic acid solution to be subjected to the $k+1^{th}$ crystallization operation, wherein the "k" is an integer 1 or more and n−1 or less. Here, the crude (meth)acrylic acid is used as the (meth)acrylic acid solution to be subjected to the first crystallization operation, and the (meth)acrylic acid melt obtained by the $n^{th}$ crystallization operation is recovered as the purified (meth)acrylic acid. In the below description, the $k^{th}$ crystallization operation may be referred to as a "$k^{th}$ stage".

In the producing process of the present invention, a constant amount $A_k$ of the (meth)acrylic acid solution is subjected to the $k^{th}$ crystallization operation. For example, the amount of the (meth)acrylic acid solution subjected to the first crystallization operation is always a constant value $A_1$, and the amount of the (meth)acrylic acid solution subjected to the second crystallization operation is always a constant value $A_2$. The values of $A_1$ and $A_2$ may be same or different from each other. When the amount of the (meth)acrylic acid solution subjected to the $k^{th}$ crystallization operation is set to be the constant value $A_k$, operation conditions of the crystallization operation at each stage are uniformed, resulting in easily conducting the crystallization operation at every stage stably. Therefore, the purity and recovered amount of the (meth)acrylic acid melt obtained at each stage is made uniform and it becomes easy to efficiently control the purity of the purified (meth)acrylic acid which is finally obtained.

For example, the case of producing purified (meth)acrylic acid from crude (meth)acrylic acid by repeating the crystallization operation three times using one crystallizer is assumed. In this case, as the number of the stage increases, purity of the (meth)acrylic acid solution subjected to the crystallization operation is enhanced, that is, the amount of impurities contained in the (meth)acrylic acid solution is decreased. Conditions of crystallization operation at the respective stages are determined appropriately, comprehensively considering factors such as time period and energy required for the crystallization operation, maximum utilization of the crystallizer performance, and the purity or recovery amount of the (meth)acrylic acid melt. Therefore, in the present case of repeating the crystallization operation three times, the amounts $A_1$, $A_2$ and $A_3$ are not necessarily identical, and rather, it is often the case that these amount values are different from each other. Similarly, also in the case of producing purified (meth)acrylic acid from crude (meth)acrylic acid multiple times, the amount of the (meth)acrylic acid solution subjected to the first crystallization operation is always set to be the constant value $A_1$, and the amounts of the (meth)acrylic acid solution subjected to the second and third crystallization operations are always set to be the constant values $A_2$ and $A_3$, respectively. As a result, even in the case where the production of purified (meth)acrylic acid from crude (meth)acrylic acid is performed multiple times, it becomes easy to maintain high purity and high recovery amounts for the obtained purified (meth)acrylic acid. Further, it becomes easy to conduct the crystallization operation of every stage stably.

In the producing process of the present invention, the constant amount $A_k$ of the (meth)acrylic acid solution is subjected to the $k^{th}$ crystallization operation and the constant amount $A_{k+1}$ of the (meth)acrylic acid solution is subjected to the $k+1^{th}$ crystallization operation, as described above; however, the amount $B_k$ of the (meth)acrylic acid melt obtained by the $k^{th}$ crystallization operation is not necessarily equal to $A_{k+1}$. Rather, $B_k$ becomes smaller than $A_{k+1}$ when the purified (meth)acrylic acid is efficiently produced by utilizing the performance of the crystallizer at a maximum. For example, in the crystallizing step, since a non-crystallized residual mother liquid, that may be hereinafter referred to as a "residual mother liquid", is separated from the (meth)acrylic acid crystal to be discharged from the crystallizer, the amount of the (meth)acrylic acid melt is reduced by the discharged amount of the residual mother liquid. In addition, in the sweating step, since a part of the (meth)acrylic acid crystal is melted and the thus obtained melt is separated from the (meth)acrylic acid melt, which is obtained in the subsequent melting step, and discharged from the crystallizer, the amount of the (meth)acrylic acid melt is reduced by the amount of the melt obtained in the sweating step. Therefore, in considering the maximum utilization of the crystallizer performance, the amount $B_k$ of the (meth)acrylic acid melt obtained by the $k^{th}$ crystallization operation tends to become insufficient relative to the amount $A_{k+1}$ of the (meth)acrylic acid solution to be subjected to the $k+1^{th}$ crystallization operation by the amounts of the residual mother liquid and the melt in the sweating step.

In the case of producing purified (meth)acrylic acid from crude (meth)acrylic acid by repeating the crystallization operation multiple times, it is efficient to perform different stages of the crystallization operation using a single crystallizer in terms of a facility aspect. However, in this kind of case, $B_k$ basically becomes an insufficient amount relative to $A_{k+1}$. Thus, it is difficult to perform the $k+1^{th}$ stage efficiently by using only the (meth)acrylic acid melt which has been obtained by the $k^{th}$ stage.

Therefore, in the present invention, storage tanks are provided in accordance with the number of times which the crystallization operation is performed, and the (meth)acrylic acid solution to be used for the $k+1^{th}$ crystallization operation is stored in a $k+1^{th}$ storage tank. Here, "k" is an integer 1 or more and n−1 or less, and therefore, n−1 storage tanks, that are from a second storage tank till an $n^{th}$ storage tank, are installed in total. The (meth)acrylic acid melt obtained by the $k^1$ crystallization operation is transferred to the $k+1^{th}$ storage tank and used for the (meth)acrylic acid solution for the $k+1^{th}$ crystallization operation.

The $k+1^{th}$ storage tank is preferably provided with a supply port through which the (meth)acrylic acid melt at the $k^{th}$ stage and the like are transferred and a discharge port through which the (meth)acrylic acid solution for the $k+1^{th}$ crystallization operation is discharged. The discharge port may be doubled as the supply port. Preferably, the supply port is provided at an upper part of the storage tank and the discharge port is provided at a lower part of the storage tank.

In the producing process of the present invention, while using the $k+1^{th}$ storage tank, the crystallization operations from the $k^{th}$ stage to the $k+1^{th}$ stage are performed as follows. That is, the (meth)acrylic acid melt obtained by the $k^{th}$ crystallization operation is utilized as the (meth)acrylic acid solution for the $k+1^{th}$ crystallization operation without being discharged from the crystallizer or is transferred from the crystallizer to the $k+1^{th}$ storage tank in accordance with the following rules (1) or (2).

Rule (1): when the amount of the (meth)acrylic acid solution stored in the k+1$^{th}$ storage tank is $A_{k+1}-B_k$ or more, the (meth)acrylic acid melt obtained by the k$^{th}$ crystallization operation is not discharged from the crystallizer and the (meth)acrylic acid solution from the k+1$^{th}$ storage tank is added to the (meth)acrylic acid melt obtained by the k$^{th}$ crystallization operation to be utilized as the (meth)acrylic acid solution for the k+1$^{th}$ crystallization operation. In this case, the (meth)acrylic acid solution stored in the k+1$^{th}$ storage tank is transferred to the crystallizer from the k+1$^{th}$ storage tank.

Rule (2): when the amount of the (meth)acrylic acid solution stored in the k+1$^{th}$ storage tank is less than $A_{k+1}-B_k$, the (meth)acrylic acid melt obtained by the k$^{th}$ crystallization operation is transferred to the k+1$^{th}$ storage tank from the crystallizer.

The rule (1) is adopted when a sufficient amount of the (meth)acrylic acid solution is stored in the storage tank. When the sufficient amount, that is, the amount stored is $A_{k+1}-B_k$ or more, of the (meth)acrylic acid solution is stored in the k+1$^{th}$ storage tank, the (meth)acrylic acid melt obtained at the k$^{th}$ stage is not discharged from the crystallizer, and the (meth)acrylic acid solution from the k+1$^{th}$ storage tank is added to the (meth)acrylic acid melt obtained by the k$^{th}$ stage in the amount of $A_{k+1}-B_k$. As a result, there exists the amount $A_{k+1}$ of the (meth)acrylic acid melt in the crystallizer, that is utilized as the (meth)acrylic acid solution for the k+1$^{th}$ stage, and the k+1$^{th}$ crystallization operation is performed.

The rule (2) is adopted when a sufficient amount of the (meth)acrylic acid solution is not stored in the storage tank. When the amount of the (meth)acrylic acid solution stored in the k+1$^{th}$ storage tank is less than $A_{k+1}-B_k$, even if the whole amount of the (meth)acrylic acid solution stored in the k+1$^{th}$ storage tank is added to the (meth)acrylic acid obtained by the k$^{th}$ stage, the total amount falls short of the necessary amount $A_{k+1}$ in the (meth)acrylic acid solution for the k$^{+1}$ stage; and hence, it may become difficult to stably perform the subsequent stages or it is likely that the quality or recovery rate of the obtained purified (meth)acrylic acid may be affected. Therefore, in this case, the (meth)acrylic acid melt obtained at the k$^{th}$ stage is transferred to the k+1$^{th}$ storage tank and subjected to another k+1$^{th}$ stage of the crystallization operation.

According to the rule (2), the (meth)acrylic acid melt obtained at the k$^{th}$ stage is transferred to the k+1$^{th}$ storage tank from the crystallizer, and thus, the crystallizer is successively utilized for performing a stage other than the k+1$^{th}$ stage. Preferably, the k$^{th}$ stage or a stage prior to the k$^{th}$ stage is performed. Thus, it is preferred that the (meth)acrylic acid melt obtained by the k$^{th}$ crystallization operation is transferred to the k+1$^{th}$ storage tank from the crystallizer, followed by performing the k$^{th}$ or less ordinal crystallization operation in the crystallizer.

At the end of the k$^{th}$ stage, the (meth)acrylic acid melt obtained at the k$^{th}$ stage, namely, the (meth)acrylic acid solution which is to be subjected to the k+1$^{th}$ stage, unavoidably partially remains within the crystallizer. In this case, when the k+2$^{th}$ stage or a stage following the k+2$^{th}$ stage is performed in the same crystallizer, the (meth)acrylic acid solution subjected to the k+2$^{th}$ stage or a stage following the k+2$^{th}$ stage is contaminated from the (meth)acrylic acid melt of the k$^{th}$ stage that remained in the crystallizer. This is not preferable from viewpoint of refinement efficiency. Therefore, in the case of following the rule (2), it is preferred that the crystallizer in which the k$^{th}$ stage has been performed is successively utilized for performing the k$^{th}$ or less ordinal crystallization operation, and as a result, the (meth)acrylic acid solution subjected to the k+2$^{th}$ stage is not contaminated by the (meth) acrylic acid melt which has been obtained at the k$^{th}$ stage and has remained within the crystallizer, whereby the purified (meth)acrylic acid is efficiently produced. More preferably, the later k$^{th}$ or less ordinal crystallization operation (that is, the k$^{th}$ or less ordinal crystallization operation but close to k$^{th}$) is performed, in viewpoint of effective utilization of the (meth)acrylic acid melt of the k$^{th}$ stage that has remained within the crystallizer.

In the case where the amount $B_k$ of the (meth)acrylic acid melt obtained by the k$^{th}$ crystallization operation is equal to $A_{k+1}$ or more than $A_{k+1}$, that is not mentioned in the above rules, it may be allowed that the (meth)acrylic acid melt obtained by the k$^{th}$ crystallization operation is transferred to the k+1$^{th}$ storage tank in an amount of $B_k-A_{k+1}$, the remaining (meth)acrylic acid melt whose amount is $A_{k+1}$ is not discharged from the crystallizer to be utilized as the (meth)acrylic acid solution for the k+1$^{th}$ crystallization operation, and then, the k+1$^{th}$ stage is performed in the crystallizer. In the case where the amount $B_k$ of the (meth)acrylic acid melt obtained by the k$^{th}$ crystallization operation is equal to $A_{k+1}$, it may be allowed that any amount of the (meth)acrylic acid melt is not discharged from the crystallizer, followed by performing the k+1$^{th}$ stage in the crystallizer. However, in the present invention, $B_k$ basically becomes less than $A_{k+1}$.

According to the producing process of the present invention, it becomes easy that the amount of (meth)acrylic acid solution to be subjected to the k$^{th}$ crystallization operation is efficiently adjusted to a constant value $A_k$ by following the above rules. Thus, it becomes possible to suppress the transferring amount of the (meth)acrylic acid melt between the crystallizer and the storage tank to a minimal necessary, resulting in suppressing energies required for pump power and the like which are related to the transfer of the (meth)acrylic acid melt. In addition, when the transferring amount of the (meth)acrylic acid melt is suppressed to a minimal necessary, the (meth)acrylic acid melt is easily prevented from inadvertent impurity incorporation, and further, production increase can be expected by reduction of transferring time of the (meth)acrylic acid melt. Therefore, the purified (meth)acrylic acid can be obtained efficiently by the crystallization operation and the purity of the obtained purified (meth)acrylic acid can be easily controlled.

In the above rules (1) and (2), the amount of the (meth) acrylic acid solution stored in the storage tank, that may be hereinafter referred to as a "store amount", is the amount that is dischargeable through pipes from the storage tank and the amount of the (meth)acrylic acid solution that can be discharged under general operating conditions. The general operating condition is given as follows. In the case of discharging the (meth)acrylic acid by a pump or the like, the general operating condition is, for example, a condition where the (meth)acrylic acid solution can be discharged by a pump by which air is not accompanied even when the liquid level in the storage tank fluctuates in some degree. This is because it is preferable that air is not accompanied with the (meth)acrylic acid solution in transferring the (meth)acrylic acid solution by a pump in viewpoint of the protection of the pump. In the case of discharging the (meth)acrylic acid by a gravity flow, the general operating condition is, for example, a condition where the (meth)acrylic acid can be discharged at not later than a predetermined flow rate; and thus, in this case, the (meth)acrylic acid solution counted in the store amount, that is stored in the storage tank, is regarded to ensure a sufficient potential energy even when its amount becomes a minimum. Specifically, the store amount is, for example, determined as follows. Here, in the below example, the storage tank is assumed to have a column shape such as a circular cylinder.

In the case where the discharge port is mounted on a bottom of the storage tank, the bottom of the storage tank is considered as reference and the amount of the (meth)acrylic acid solution stored above the reference is regarded as the store amount. Or, a somewhat upper position from the bottom of the storage tank is considered as reference and the amount of the (meth)acrylic acid solution stored above the reference is regarded as the store amount, in order that (meth)acrylic acid solution is smoothly discharged from the bottom and air is prevented from being accompanied.

In the case where the discharge port is mounted on a wall of the storage tank and the (meth)acrylic acid solution is transferred from the storage tank to the crystallizer by a pump, an upper rim of the discharge port on the wall of the storage tank is considered as reference and the amount of the (meth)acrylic acid solution stored above the reference is regarded as the store amount. Or, a somewhat upper position from the upper rim of the discharge port is considered as reference and the amount of the (meth)acrylic acid solution stored above the reference is regarded as the store amount, in order that air is not accompanied by a pump even when the liquid level in the storage tank fluctuates in some degree.

In the case where the discharge port is mounted on a wall of the storage tank and the (meth)acrylic acid solution is transferred from the storage tank to the crystallizer by a gravity flow, a lower rim of the discharge port on the wall of the storage tank is considered as reference and the amount of the (meth)acrylic acid solution stored above the reference is regarded as the store amount. Or, a somewhat upper position from the lower rim of the discharge port is considered as reference and the amount of the (meth)acrylic acid solution which is stored above the reference is regarded as the store amount, in order that the (meth)acrylic acid solution is discharged at not later than a predetermined flow rate.

In the case where the discharge port having a downward opening is provided within the storage tank, an upper rim of the discharge port or a somewhat upper position therefrom is considered as reference and the amount of the (meth)acrylic acid solution stored above the reference is regarded as the store amount. For example, this case is applied when a submerged pump is installed within the storage tank.

In the crystallization operation, the (meth)acrylic acid melt which has been purified is obtained, whereas low purity (meth)acrylic acid is obtained besides the (meth)acrylic acid melt. For example, a residual mother liquid which is a remained non-crystallized (meth)acrylic acid solution in the crystallizing step corresponds to the low purity (meth)acrylic acid. In addition, a melt which is obtained by washing away impurities present between the crystals or on the surface of the crystal in the sweating step also corresponds to the low purity (meth)acrylic acid. This kind of the low purity (meth)acrylic acid is preferably treated as follows. That is, the low purity (meth)acrylic acid obtained at the $k^{th}$ stage is transferred to the $k^{th}$ storage tank or the $k-1^{th}$ or less ordinal storage tank which deals with lower purity (meth)acrylic acid, since it contains less amount of (meth)acrylic acid relative to the (meth)acrylic acid solution subjected to the $k^{th}$ stage. Preferably, the low purity (meth)acrylic acid obtained at the $k^{th}$ stage is transferred to the $k-1^{th}$ or less ordinal storage tank, and more preferably, transferred to the $k-1^{th}$ storage tank. The low purity (meth)acrylic acid obtained at the first stage is preferably returned to any step prior to the crystallization.

Next, the producing process of the present invention is explained referring to FIG. 1. FIG. 1 shows a process for producing purified (meth)acrylic acid from crude (meth)acrylic acid by repeating the crystallization operation three times using one crystallizer. However, the producing process of the present invention is not limited to the following embodiment.

A crystallizer 1 for performing the crystallization operation is performed has a heat-transfer surface 2. Into the crystallizer 1, a (meth)acrylic acid solution is supplied through an inlet 3 of the crystallizer. In a crystallizing step, the (meth)acrylic acid solution is cooled via the heat-transfer surface 2 to generate a (meth)acrylic acid crystal. In a melting step, the (meth)acrylic acid crystal is heated via the heat-transfer surface 2, thereby obtaining a (meth)acrylic acid melt. The (meth)acrylic acid melt is discharged from the crystallizer 1 through an outlet 4 of the crystallizer.

Two storage tanks, that is, a second storage tank 12 for storing the (meth)acrylic acid solution used in a second crystallization operation and a third storage tank 13 for storing the (meth)acrylic acid solution used in a third crystallization operation, are installed. The (meth)acrylic acid solution used in a first crystallization operation, namely, crude (meth)acrylic acid, is stored in a raw material tank 11.

In each of the crystallization operations, the (meth)acrylic acid solution is fed to the crystallizer 1 from the raw material tank 11, the second storage tank 12 or the third storage tank 13, and the (meth)acrylic acid solution is crystallized and the crystallized (meth)acrylic acid is melted to obtain the (meth)acrylic acid melt. The (meth)acrylic acid melt which has been obtained by the first crystallization operation is utilized as the (meth)acrylic acid solution for the second crystallization operation without being discharged from the crystallizer 1 or is transferred to the second storage tank 12 depending on the store amount of the (meth)acrylic acid solution in the second storage tank 12. The (meth)acrylic acid melt which has been obtained by the second crystallization operation is utilized as the (meth)acrylic acid solution for the third crystallization operation without being discharged from the crystallizer 1 or is transferred to the third storage tank 13 depending on the store amount of the (meth)acrylic acid solution in the third storage tank 13. The (meth)acrylic acid melt which has been obtained by the third crystallization operation is discharged to the outside the system through a path 14 to be recovered as purified (meth)acrylic acid.

Here, the producing process of the present invention is explained in detail, taking as an example the second crystallization operation, namely, the second stage. At the second stage, the amount $A_2$ of the (meth)acrylic acid solution is crystallized and melted in the crystallizer 1 to obtain the (meth)acrylic acid melt in the amount of $B_2$. A residual mother liquid generated in the crystallizing step of the second stage and a melt generated in the sweating step of the second stage are discharged from the crystallizer 1 before the melting step and is transferred to, for example, the raw material tank 11.

The amount of the (meth)acrylic acid solution to be subjected to the third stage is $A_3$. Meanwhile, when the amount of the (meth)acrylic acid solution stored in the third storage tank 13 is $A_3-B_2$ or more, the (meth)acrylic acid melt obtained at the second stage is not discharged from the crystallizer 1 and the (meth)acrylic acid solution stored in the third storage tank 13 is added to the (meth)acrylic acid melt in the amount of $A_3-B_2$ to be utilized as the (meth)acrylic acid solution for the third stage.

When the amount of the (meth)acrylic acid solution stored in the third storage tank 13 is less than $A_3-B_2$, the (meth)

acrylic acid melt obtained at the second stage is transferred to the third storage tank 13 from crystallizer 1. In this case, after transferring the (meth)acrylic acid melt obtained by the second stage is transferred to the third storage tank 13 from crystallizer 1, the second stage is performed in the crystallizer 1, if the second stage is practicable. That is, when the amount of the (meth)acrylic acid solution stored in the second storage tank is $A_2$ or more, the (meth)acrylic acid solution stored in the second storage tank is transferred to the crystallizer 1 in the amount of $A_2$ to conduct the second stage in the crystallizer 1. When amount of the (meth)acrylic acid solution stored in the second storage tank is less than $A_2$, the first stage is conducted in the crystallizer 1.

The producing process of the present invention can be applied to both the case where one crystallizer is provided and the case where two or more crystallizers are provided. In the case of providing a plurality of crystallizers, the plurality of crystallizers may share one each of the storage tanks. Thus, the number of the storage tank does not depend of the number of the crystallizers but depends on the number of times of the crystallization operation.

In the case where a plurality of crystallizers are provided, the amount of the (meth)acrylic acid solution subjected to the $k^{th}$ stage is preferably set to be a constant value $A_k$ in the every crystallizer. When operation conditions of each stage are uniformed among all the crystallizers, the (meth)acrylic acid melt having a uniform quality can be easily obtained in each stage even in the case where each stage is performed in any crystallizer. Moreover, when all the crystallizers share each of the storage tanks, it becomes possible to efficiently produce the purified (meth)acrylic acid from the crude (meth)acrylic acid while utilizing the crystallizer performance at a maximum.

In the case where a plurality of crystallizers are provided, the crystallization operations are preferably performed such that ending times of the crystallization operations become different from each other. Assuming that two crystallizers are used, it is preferable that while the crystallizing step is performed in one crystallizer, the sweating step and the melting step are performed in the other crystallizer, for example. Performing the crystallization operations such that the ending times of the crystallization operations are different from each other allows capacity of the storage tank not to be enlarged excessively. For example, if the crystallization operations in two crystallizers are completed simultaneously, a case where the (meth)acrylic acid melts from the two crystallizers are simultaneously transferred to one storage tank possibly occurs, and therefore, it is needed that a storage tank having such a capacity that the (meth)acrylic acid melts obtained from two crystallizers can be accepted at a minimum is installed. Meanwhile, in the case where the crystallization operations in two crystallizers are completed such that the ending times thereof are different from each other, a storage tank having such a capacity that the (meth)acrylic acid melt obtained from one crystallizer can be accepted at a minimum needs to be installed.

The process for producing (meth)acrylic acid of the present invention preferably further comprises the step of obtaining the crude (meth)acrylic acid. The step of obtaining the crude (meth)acrylic acid preferably includes a gas-phase catalytic oxidation step of producing (meth)acrylic acid-containing gas from a (meth)acrylic acid production raw material by gas-phase catalytic oxidation and a collection step of collecting the (meth)acrylic acid-containing gas with a liquid medium. In addition, a condensation step of condensing the (meth)acrylic acid-containing gas to be collected may be employed, instead of the collection step. Further, for the purpose of increasing (meth)acrylic acid content in the (meth)acrylic acid solution obtained by the collection step or the condensation step, a purification step may be provided after the collection step or the condensation step.

In the gas-phase catalytic oxidation step, propane, propylene, (meth)acrolein, isobutylene, or the like is used as the (meth)acrylic acid production raw material, and the (meth)acrylic acid production raw material undergoes gas-phase catalytic oxidation by molecular oxygen to produce the (meth)acrylic acid-containing gas. The gas-phase catalytic oxidation is preferably carried out using a conventionally-known oxidation catalyst.

In the collection step, the (meth)acrylic acid-containing gas obtained by the gas-phase catalytic oxidation step is collected with a liquid medium in a collection column to obtain the (meth)acrylic acid solution. Examples of the liquid medium include water, (meth)acrylic acid-containing water, a high boiling point solvent (e.g. diphenyl ether, biphenyl and the like), and the like. In the present invention, the (meth)acrylic acid solution obtained by the collection step may be subjected to the crystallization operation as the crude (meth)acrylic acid. In addition, the (meth)acrylic acid solution obtained by condensing the (meth)acrylic acid-containing gas may be subjected to the crystallization operation as the crude (meth)acrylic acid.

EXAMPLES

The present invention is hereinafter described more specifically by reference to Examples; however, the scope of the present invention is not limited to these Examples.

Producing Example 1

Purified acrylic acid was produced from crude acrylic acid by repeating a crystallization operation, in which an acrylic acid solution was crystallized and the crystallized acrylic acid was melted to obtain an acrylic acid melt, three times. The crystallization operation was conducted using one crystallizer, and further, a raw material tank, a second storage tank and a third storage tank were installed. The amounts of the acrylic acid solution subjected to the respective crystallization operations were 5.5 ton ($=A_1$) for a first crystallization operation (a first stage), 6.8 ton ($=A_2$) for a second crystallization operation (a second stage), and 7.1 ton ($=A_3$) for a third crystallization operation (a third stage). In every crystallization operation, a crystallizing step of obtaining an acrylic acid crystal by crystallizing the acrylic acid solution, a sweating step of obtaining a sweated melt by partially-melting the acrylic acid crystal, and a melting step of obtaining the acrylic acid melt by melting the acrylic acid crystal were carried out in this order.

Before the start of the crystallization, 3.0 ton of the acrylic acid solution was stored in the second storage tank and 3.0 ton of the acrylic acid solution was also stored in the third storage tank. In the raw material tank, 30.0 ton of the crude acrylic acid was stored.

At the first stage, 5.5 ton of the crude acrylic acid was supplied to the crystallizer as the acrylic acid solution, and subjected to the crystallizing step, the sweating step and the melting step, thereby obtaining 3.8 ton ($=B_1$) of the acrylic acid melt. At the first stage, a total amount of a residual mother liquid generated in the crystallizing step and the sweated melt generated in the sweating step was 1.7 ton, and these were transferred to a step prior to the crystallization.

The amount of the acrylic acid solution stored in the second storage tank was 3.0 ton, which amount was equal to $A_2-B_1=3.0$ ton. Therefore, the acrylic acid solution obtained by the first stage was not discharged from the crystallizer, 3.0 ton of the acrylic acid solution from the second storage tank was added to the acrylic acid solution, and thus obtained 6.8 ton of the acrylic acid solution was used for performing the second stage. At the second stage, the crystallizing step, the sweating step and the melting step were performed, thereby obtaining 4.7 ton ($=B_2$) of the acrylic acid melt. At the second stage, the total amount of the residual mother liquid generated in the crystallizing step and the sweated melt generated in the sweating step was 2.1 ton, and these were transferred to the raw material tank.

The amount of the acrylic acid solution stored in the third storage tank was 3.0 ton, which amount was equal to or more than $A_3-B_2=2.4$ ton. Therefore, the acrylic acid solution obtained by the second stage was not discharged from the crystallizer, 2.4 ton of the acrylic acid solution from the third storage tank was added to the acrylic acid solution, and thus obtained 7.1 ton of the acrylic acid solution was used for performing the third stage. At the third stage, the crystallizing step, the sweating step and the melting step were performed, thereby obtaining 4.6 ton ($=B_3$) of the acrylic acid melt, that was transferred to a product tank as the purified (meth)acrylic acid. At the third stage, the total amount of the residual mother liquid generated in the crystallizing step and the sweated melt generated in the sweating step was 2.5 ton, and these were transferred to the second storage tank.

After performing the above crystallization, the store amount of the crude acrylic acid in the raw material tank was 26.6 ton, the store amount of the acrylic acid solution in the second storage tank was 2.5 ton, and the store amount of the acrylic acid solution in the third storage tank was 0.6 ton. The store amount of the acrylic acid solution in the third storage tank was less than 7.1 ton ($=A_3$) of the supply amount of the acrylic acid solution at the third stage, and the store amount of the acrylic acid solution in the second storage tank was less than 6.8 ton ($=A_2$) of the supply amount of the acrylic acid solution at the second stage; and hence, the first stage was successively conducted in the crystallizer.

At the second time first stage, 5.5 ton of the crude acrylic acid was supplied to the crystallizer from the raw material tank, and subjected to the crystallizing step, the sweating step and the melting step, thereby obtaining 3.8 ton ($=B_1$) of the acrylic acid melt. In the second storage tank, 2.5 ton of the acrylic acid solution was stored, which amount was less than $A_2-B_1=3.0$ ton, and therefore, the acrylic acid melt obtained by the second time first stage was transferred to the second storage tank. In the crystallizer, the third time first stage was successively conducted.

As the result of repeating the crystallization operation of the above, lengths of time required to the crystallization operation, that included from the crystallizing step to the melting step, in the first time first stage and the first time second stage were respectively 105 minutes. Meanwhile, in the first time third stage and the second time first stage, it took a long time to discharge the acrylic acid melt from the crystallizer, and as a result, lengths of time required to the crystallization operation, that included from the crystallizing step to the melting step, were respectively 110 minutes.

Producing Example 2

The first time first stage to the first time third stage were conducted in the crystallizer in the same manner as the producing example 1, except that the 10.0 ton of the acrylic acid solution was stored in the third storage tank before the start of the crystallization. After performing the crystallization, the store amount of the crude acrylic acid in the raw material tank was 26.6 ton, the store amount of the acrylic acid solution in the second storage tank was 2.5 ton, and the store amount of the acrylic acid solution in the third storage tank was 7.6 ton. Successively, the second time first stage and the latter stage thereof were conducted.

At the second time first stage, 5.5 ton of the crude acrylic acid was supplied to the crystallizer from the raw material tank, and subjected to the crystallizing step, the sweating step and the melting step, thereby obtaining 3.8 ton ($=B_1$) of the acrylic acid melt. In the second storage tank, 2.5 ton of the acrylic acid solution was stored, which amount was less than $A_2-B_1=3.0$ ton, and therefore, the acrylic acid melt obtained by the second time first stage was transferred to the second storage tank from the crystallizer.

Next, 7.1 ton of the acrylic acid solution from the third storage tank was transferred to the crystallizer, and the second time third stage was conducted. At the third stage, the crystallizing step, the sweating step and the melting step were performed, thereby obtaining 4.6 ton ($=B_3$) of the acrylic acid melt, that was transferred to the product tank as the purified (meth)acrylic acid. At the third stage, the total amount of the residual mother liquid generated in the crystallizing step and the sweated melt generated in the sweating step was 2.5 ton, and these were transferred to the second storage tank.

As the result of repeating the crystallization operation of the above, lengths of time required to the crystallization operation, that included from the crystallizing step to the melting step, in the first time first stage and the first time second stage were respectively 105 minutes. Meanwhile, in the first and second times third stage and the second time first stage, it took a long time to discharge the acrylic acid melt from the crystallizer, and as a result, lengths of time required to the crystallization operation, that included from the crystallizing step to the melting step, were respectively 110 minutes. When compared between the products obtained by the first time third stage and the second time third stage, the products obtained by the second time third stage contained slightly larger amount of impurities.

Producing Example 3

Purified acrylic acid was produced from crude acrylic acid in the same manner as the producing example 1, except that after all of the acrylic acid melt obtained by each stage was transferred to the corresponding storage tank, a predefined amount of the (meth)acrylic acid solution for each stage was transferred from the storage tank to the crystallizer, thereby performing the crystallization operation of the subsequent stage. Specifically, the crystallization operation of every stage was performed as follows.

At the first stage, 5.5 ton of the crude acrylic acid was supplied to the crystallizer as the acrylic acid solution, and subjected to the crystallizing step, the sweating step and the melting step, thereby obtaining 3.8 ton ($=B_1$) of the acrylic acid melt. The acrylic acid melt obtained by the first stage was wholly transferred to the second storage tank. In the second storage tank, since 3.0 ton of the acrylic acid solution had been stored from the beginning, the acrylic acid melt transferred from the crystallizer was incorporated with it, whereby the store amount of the acrylic acid solution in the second storage tank became 6.8 ton. 1.7 ton of the total amount of the residual mother liquid generated in the crystallizing step and the sweated melt generated in the sweating step was transferred to a step prior to the crystallization.

At the second stage, 6.8 ton of the acrylic acid solution from the second storage tank was supplied to the crystallizer, and subjected to the crystallizing step, the sweating step and the melting step, thereby obtaining 4.7 ton (=$B_2$) of the acrylic acid melt. The acrylic acid melt obtained by the second stage was wholly transferred to the third storage tank. In the third storage tank, since 3.0 ton of the acrylic acid solution had been stored from the beginning, the acrylic acid melt transferred from the crystallizer was incorporated with it, whereby the store amount of the acrylic acid solution in the third storage tank became 7.7 ton. The total amount of the residual mother liquid generated in the crystallizing step and the sweated melt generated in the sweating step was 2.1 ton, and these were transferred to the raw material tank.

At the third stage, 7.1 ton of the acrylic acid solution from the third storage tank was supplied to the crystallizer, and subjected to the crystallizing step, the sweating step and the melting step, thereby obtaining 4.6 ton (=$B_3$) of the acrylic acid melt, that was transferred to the product tank as the purified (meth)acrylic acid. The total amount of the residual mother liquid generated in the crystallizing step and the sweated melt generated in the sweating step was 2.5 ton, and these were transferred to the second storage tank.

After performing the above crystallization, the second and third storage tanks did not contain sufficient amounts of the acrylic acid solution required for the respective stages, and hence, the first stage was successively conducted in the crystallizer.

At the second time first stage, 5.5 ton of the crude acrylic acid was supplied to the crystallizer from the raw material tank, and subjected to the crystallizing step, the sweating step and the melting step, thereby obtaining 3.8 ton (=$B_1$) of the acrylic acid melt. The acrylic acid melt obtained by the second time first stage was wholly transferred to the second storage tank. In the crystallizer, the third time first stage was successively performed.

In the producing example 3, as the result of repeating the crystallization operation of the above, it took a long time to discharge the acrylic acid melt from the crystallizer in every stage, and thus, lengths of time required to the crystallization operation, that included from the crystallizing step to the melting step, were respectively 110 minutes. In the producing example 3, transferring amounts of the acrylic acid melt and the acrylic acid solution increased and operating time of a pump became long as compared to the producing example 1.

INDUSTRIAL APPLICABILITY

The present invention can be used for a process for producing (meth)acrylic acid having the crystallization operations.

EXPLANATION OF REFERENCE

1: crystallizer
11: raw material tank
12: second storage tank
13: third storage tank

The invention claimed is:

1. A process for producing (meth)acrylic acid, comprising the step of repeating a crystallization operation n times, wherein n is an integer of 2 or more, to produce purified (meth)acrylic acid from crude (meth)acrylic acid, wherein a (meth)acrylic acid solution is crystallized and the crystallized (meth)acrylic acid is melted to obtain a (meth)acrylic acid melt in the crystallization operation;

wherein a constant amount $A_k$ of the (meth)acrylic acid solution is subjected to the $k^{th}$ crystallization operation, wherein k is an integer 1 or more and n−1 or less, and the (meth)acrylic acid melt obtained by the $k^{th}$ crystallization operation is utilized as the (meth)acrylic acid solution for the $k+1^{th}$ crystallization operation without being discharged from a crystallizer or is transferred from the crystallizer to a $k+1^{th}$ storage tank for storing the (meth)acrylic acid solution to be used in the $k+1^{th}$ crystallization operation in accordance with the following Rules (1) or (2):

Rule (1): when an amount of the (meth)acrylic acid melt obtained by the $k^{th}$ crystallization operation is $B_k$ and an amount of the (meth)acrylic acid solution stored in the $k+1^{th}$ storage tank is $A_{k+1}-B_k$ or more, the (meth)acrylic acid melt obtained by the $k^{th}$ crystallization operation is not discharged from the crystallizer and the (meth)acrylic acid solution from the $k+1^{th}$ storage tank is added to the (meth)acrylic acid melt obtained by the $k^{th}$ crystallization operation to be utilized as the (meth)acrylic acid solution for the $k+1^{th}$ crystallization operation; and Rule (2): when the amount of the (meth)acrylic acid solution stored in the $k+1^{th}$ storage tank is less than $A_{k+1}-B_k$, the (meth)acrylic acid melt obtained by the $k^{th}$ crystallization operation is transferred to the $k+1^{th}$ storage tank from the crystallizer.

2. The process for producing (meth)acrylic acid according to claim 1, wherein when the amount of the (meth)acrylic acid solution stored in the $k+1^{th}$ storage tank is less than $A_{k+1}-B_k$, the (meth)acrylic acid melt obtained by the $k^{th}$ crystallization operation is transferred to the $k+1^{th}$ storage tank from the crystallizer, followed by performing the $k^{th}$ or less ordinal crystallization operation in the crystallizer.

3. The process for producing (meth)acrylic acid according to claim 1, wherein when the amount of the (meth)acrylic acid solution stored in the $k+1^{th}$ storage tank is $A_{k+1}-B_k$ or more, the (meth)acrylic acid melt obtained by the $k^{th}$ crystallization operation is not discharged from the crystallizer and an amount $A_{k+1}-B_k$ of the (meth)acrylic acid solution from the $k+1^{th}$ storage tank is added to the (meth)acrylic acid melt obtained by the $k^{th}$ crystallization operation.

4. The process for producing (meth)acrylic acid according to claim 2, wherein when the amount of the (meth)acrylic acid solution stored in the $k+1^{th}$ storage tank is $A_{k+1}-B_k$ or more, the (meth)acrylic acid melt obtained by the $k^{th}$ crystallization operation is not discharged from the crystallizer and an amount $A_{k+1}-B_k$ of the (meth)acrylic acid solution from the $k+1^{th}$ storage tank is added to the (meth)acrylic acid melt obtained by the $k^{th}$ crystallization operation.

* * * * *